United States Patent [19]
Saniez et al.

[11] Patent Number: 5,902,615
[45] Date of Patent: May 11, 1999

[54] NUTRITIONAL COMPOSITION RESULTING FROM MAIZE STEEPING

[75] Inventors: Marie Hélène Saniez, Saint Andre; Thomas Erpicum, Richebourg, both of France

[73] Assignee: Roquette Freres, Lestrem, France

[21] Appl. No.: 08/895,631

[22] Filed: Jul. 17, 1997

[30] Foreign Application Priority Data

Jul. 18, 1996 [FR] France .................................. 96 09015

[51] Int. Cl.$^6$ ........................... A23B 7/155; C07G 17/00; A61K 38/48
[52] U.S. Cl. ................................. 426/51; 426/18; 426/31; 426/49; 426/52; 426/53; 426/54; 435/170; 435/272; 435/267; 424/93.45; 424/94.63; 424/94.6; 424/94.2; 424/195.1
[58] Field of Search ...................... 435/272, 267, 435/170; 426/18, 31, 49, 51, 52, 53, 54; 424/93.45, 94.63, 94.6, 94.2, 195.1

[56] References Cited

U.S. PATENT DOCUMENTS

| 4,086,135 | 4/1978 | Balana et al. ............................ 435/275 |
| 4,359,528 | 11/1982 | Devos et al. . |
| 4,914,029 | 4/1990 | Caransa et al. . |

FOREIGN PATENT DOCUMENTS

| 0724841 | 8/1996 | European Pat. Off. . |
| 2254641 | 7/1975 | France . |
| 4198080 | 7/1992 | Japan . |
| 1387998 | 3/1975 | United Kingdom . |
| WO 93/16175 | 8/1993 | WIPO . |

OTHER PUBLICATIONS

Chemical abstracts, vol. 117, No. 21, Nov. 23, 1992 Abstract No. 211601 & JP 04 198 080 (Mitsui Toatsu Chemicals, Inc.) Jul. 17, 1992.
Analysis Biochemistry (1976) 72, 248.
Manuel d'Analyse Chimique Volumétrique, H. Mathieu, Zd. Masson, 1946, p. 398.
Article by M.L. Anson published in 1939 in Gen. Physiol. 22, pp. 79–89.

*Primary Examiner*—Francisco Prats
*Attorney, Agent, or Firm*—Larson & Taylor

[57] ABSTRACT

The invention relates to a new nutritional composition resulting from maize steeping. This composition comprises an inorganic phosphorous concentration to total phosphorus concentration ratio (Pi/Pt) of between 35 and 95%. The composition also comprises proteins in an amount which gives a value of less than or equal to 5 according to a C test and reducing substances in an amount which gives a value of less than or equal to 0.9% in the BERTRAND method. A process for producing a nutritional composition is also disclosed, wherein the process requires maize steepwater to be subjected to a treatment with the aid of protease and phytase enzymes in the presence of lactic acid bacteria. Furthermore, the enzymatic treatment is performed on a steepwater whose dry matter content is between 5 and 25%, and Ph between 3 and 5, at a temperature varying between 40 and 50° C. and for 4 to 16 hours.

12 Claims, No Drawings

NUTRITIONAL COMPOSITION RESULTING FROM MAIZE STEEPING

The present invention relates to an improved nutritional composition which results from steeping maize.

It also relates to the process for obtaining such a composition and to the application of the composition as a culture medium in fermentation industries, as a nutrient or alimentary additive in compositions intended for humans or animals, and as an agent which is of value for preparing fertilizers which are intended for plants.

Maize steeping is the first step in the extraction of starch in a wet starch factory. It consists in maintaining the maize, which is located in silos, for a given time in warm water which contains a low quantity of sulphur dioxide, with the purpose of the latter being to facilitate the subsequent separation of the proteins, cellulose and starch and otherwise to prevent growth of undesirable microorganisms.

During this operation, two essential phenomena take place simultaneously. On the one hand, the highly fermentable soluble substances which are contained in the maize kernels are transferred into the steeping water. On the other hand, the steeping conditions (presence of sulphites and free reducing sugars, and temperature level) are favourable for the rapid development of bacteria, in the main lactic acid bacteria.

The principal interest of steeping water, commonly termed "corn steep" by the skilled person, stems from the fact that it is composed of essential compounds which derive from the transfer of these soluble substances. These compounds constitute factors which are favourable both to the growth of microorganisms and to the production of secondary metabolites, and make the steeping water an ideal source of nutritional substances for fermentation industries.

Thus, readily assimilable carbon sources which are present in the corn steep are: sugars and organic acids, as sources of nitrogen and carbon: amino acids and polypeptides and, as sources of trace elements which are necessary for the growth of microorganisms: "buffering" agents and minerals.

In addition, corn steep constitutes a substrate which is relatively inexpensive as compared with the yeast extracts which represent the reference material in this area and which are used both in human and animal nutrition.

Moreover, it is known that the use of corn steep makes it possible, by replacing complex nitrogen sources such as cotton or soya bean proteins, to increase substantially the production yields of antibiotics.

For use in fermentation, the corn steep should be subjected to a prior sterilization whose temperature and pH conditions and whose duration are chosen in order to ensure microorganism destruction. Thus, the temperature is generally between 105 and 130° C. and the pH varies between 3.0 and 8.0. However, these temperature and pH conditions cause some of the constituents of the corn steep to precipitate, resulting in a large number of drawbacks.

Thus, the use of such a non-homogenous corn steep leads to problems when it is being prepared and, in particular, when it is being concentrated. Furthermore, the use of such a corn steep results in the formation of a substantial deposit on the fermenter walls, which deposit risks clogging the heat exchangers. Finally, recovery of the fermentation products can be seriously disrupted as a result of membranes and filters becoming clogged.

Moreover, the presence of free reducing substances in the corn steep leads to the product becoming coloured to a significant extent during sterilization and concentration operations, with this coloration resulting in a decrease in the availability of some of the nutritional substances which the product contains.

In addition, these free reducing substances make the product microbiologically unstable by promoting the growth of yeasts during storage of the product.

Among the solutions proposed for resolving the problem of the heterogeneity of corn steep, the oldest is that which consists in extracting the substances which are responsible for the coagulation from the corn steep by chemical precipitation. Thus, it is known to add alkaline agents (lime, sodium hydroxide solution, etc.) or metallic compounds (in particular aluminium salts) to the corn steep in order to precipitate certain proteins, sulphite or sulphate compounds or else phytic acid. However, apart from the extra cost associated with this additional treatment, its major drawback is the removal of nutritional substances from the medium. Furthermore, such a treatment necessitates introducing chemical products into the corn steep in quantities which can be substantial, thereby noticeably modifying its composition and thus limiting its potential uses.

Ultrafiltration has also been resorted to for the purpose of separating the heat-coagulable molecular species, in particular proteins and peptides, from the maize-steeping water. This technique has, moreover, been the subject of a French patent, No. 2 140 672, which was granted to SCHOLTEN-HONIG RESEARCH.

Finally, it has more recently been proposed to treat corn steep with enzymes.

Thus, U.S. Pat. No. 4 914 029, granted to DORR-OLIVER, describes treatment with a phytase/cellulase mixture.

However, if such a treatment makes it possible to avoid precipitating the phytic acid, it is not adequate to solve completely the problem of the formation of a precipitate during the sterilization of the corn steep.

Besides this, Japanese Patent No. 04-198 080, which was filed by MITSUI TOATSU CHEMICALS, describes treating with a protease: the action of an enzyme of this nature on corn steep contributes to improving the filterability of the corn steep. The corn steep which has been treated in this way is intended for preparing a liquid fertilizer.

Similarly, M. ROUSHDI, Y. GHALI and A. HASSANEAN have studied the action of two proteolytic enzymes (the Alkalase and the Neutrase which are manufactured by NOVO) on maize-steeping water with a view to reducing the duration of the steeping operation and obtaining a starch which has a reduced content of protein.

Nevertheless, it was apparent that treating corn steep with a proteolytic enzyme was not sufficient to eliminate the abovementioned problems satisfactorily.

French Patent No. 2 254 641, which was filed by CPC INTERNATIONAL, suggested adding lactic acid bacteria to the steeping water during the steeping process with the sole aim of reducing the duration of the process. It was noticed that a decrease in the content of reducing sugars in the steeping water was then obtained at the same time, with this content changing from 6.5% to 1.7–1.9%.

However, none of the treatments which have been described and which have been put into operation up to the present time has made it possible to resolve satisfactorily the problem of the loss of a not insignificant fraction of the constituents of the corn steep, and therefore of its nutritional qualities, whether by formation of a precipitate or by the appearance of a pronounced coloration during its sterilization, or by a change in the appearance of the product and in particular its colour, and its microbiological qualities, during its storage.

The applicant has now developed a corn steep whose nutritional qualities are improved, which is resistant to the thermal treatment which is necessitated by its use as a fermentation medium or as an additive in human or animal nutrition, and which displays optimum microbiological stability.

In addition, this nutritional composition exhibits the advantage of being able to be concentrated to greater than 60% dry matter without coming up against a caking phenomenon as in the case of the corn steep of the prior art. Such a concentration endows the nutritional composition according to the invention with a microbiological stability which is even more improved and with a viscosity which is perfectly adapted to industrial implementation conditions such as, in particular, transfer using pumps. It also exhibits an economic advantage due to a reduction in storage and transport costs and also costs engendered by the evaporation step. Thus, clogging of the corn steep evaporator heaters is a significant problem, the only current solution to which is that of cleaning the evaporators and the piping by employing sodium hydroxide solution and nitric acid.

This economic advantage is also appreciable at the step of drying dry feeds for animals, which feeds are obtained from a composition according to the invention, for example by incorporating this composition into dry spent-maize grains.

In this case, an ecological importance is added to the economic advantage since the olfactory pollution which is associated with the drying is markedly reduced.

The invention therefore relates, first and foremost, to a nutritional composition which is characterized by the fact that it exhibits an inorganic phosphorus concentration to total phosphorus concentration ratio which is between 35 and 95%, in that assay of the proteins which it contains, which assay is carried out using a C test, gives a value which is less than or equal to 5, preferably less than or equal to 1, and even more preferably less than or equal to 0.5, and in that its content of total reducing substances is less than or equal to 0.9%.

The concentrations of inorganic phosphorus and total phosphorus are measured by known methods such as those described below.

With regard to the inorganic phosphorus, the method of reference consists in measuring the absorbance, at a wavelength of 360 nm, of a complex which is obtained by reacting the inorganic phosphorus with ammonium molybdate, with the absorbance being directly proportional to the quantity of inorganic phosphorus which is present in the sample. This method can be carried out by, for example, using the assay kit which is marketed by GILFORD DIAGNOSTICS under reference No. 722058.

The total phosphorus is assayed by the ISO 3946 standard method, which is based on the same principle as that applied to the determination of the concentration of inorganic phosphorus, as described above. However, a preliminary step is carried out which consists in destroying the organic components of the products to be assayed by mineralizing with a mixture of sulphuric and nitric acids and transforming the phosphates into orthophosphates. The following steps consist in forming the complex with molybdenum and then measuring the absorbance at a wavelength of 825 nm.

Preferably, the concentration of inorganic phosphorus to concentration of total phosphorus ratio (Pi/Pt) is between 60 and 95%, and even more preferably between 75 and 85%.

The aim of the C test which is applied to the compositions according to the invention is that of measuring the protein concentration per 100 grams of dry matter of the supernatant of these compositions.

In order to do this, these supernatants are measured spectrophotometrically in the presence of a coloured reagent in accordance with the Bradford method, which method is known for assaying proteins and described, in particular, in Analytical Biochemistry (1976), 72, 248.

In the present case, the reagent which is employed is Coomassie Brilliant Blue G 250, which reagent is manufactured by PIERCE under reference No. 23200 and has the characteristic of binding in acid solution to proteins and peptides of more than 20 amino acids, with this binding being accompanied by a colour change from reddish brown to blue.

The concentration of protein in the supernatants of the compositions is determined by measuring the absorbance at a wavelength of 595 nm, which absorbance corresponds to the amount of reagent which is bound to the proteins which are present and is consequently proportional to the quantity of protein, and then comparing with a calibration curve which is obtained for different concentrations of a standard protein (bovine serum albumin, Ref. No. 23209 from PIERCE).

In order to carry out this measurement, the nutritional composition to be tested is first of all brought to a dry matter content of 30% by weight. The composition is then centrifuged at 5000 g for 15 min and the supernatant is recovered and brought to a dry matter content of 25% by weight. The Bradford method is then applied to this supernatant by introducing the coloured reagent, mixing and then reading the absorbance.

The value which is obtained, and which corresponds to the protein concentration in grams per liter of supernatant, is then converted to a concentration in grams per 100 g of supernatant dry matter.

The nutritional compositions which are the subject of the present invention are such that the protein concentration in grams per 100 g of supernatant dry matter is less than or equal to 5, and preferably less than or equal to 1. Even more preferably, the compositions according to the invention will exhibit a protein concentration in grams per 100 g of supernatant dry matter which is less than or equal to 0.5.

In order to measure the content of total reducing substances in a nutritional composition according to the invention, the latter is subjected to acid hydrolysis by boiling it for 1 hour in the presence of hydrochloric acid in order to hydrolyse the polysaccharides and oligosaccharides which are present. The totality of reducing substances is then assayed using the BERTRAND method as described, in particular, in the "Manuel d'analyse chimique volumetrique (Manual of volumetric chemical analysis)", H. MATHIEU, Ed. MASSON, 1946, p. 398, in accordance with the following principle:

The solution containing the reducing substances is heated with an excess of copper/sodium reagent, resulting in the precipitation of cuprous oxide in a quantity which is proportional to the concentration of reducing substances which are present in the solution. This precipitate, when brought into contact with a solution of ferric sulphate in sulphuric acid, reduces part of the ferric salt to ferrous sulphate. The ferrous sulphate is then assayed with a $KMnO_4$ solution of known titre, thereby making it possible to deduce the corresponding quantity of cuprous oxide and therefore the quantity of reducing substances which was initially present in the solution.

The content of total reducing substances therefore includes, at one and the same time, that of free reducing substances and that of reducing substances which are capable of being released.

Thus, if the free reducing substances contribute, as previously explained, to the physical and microbiological instability of the compositions, the presence of reducing substances which are capable of being released represents an undoubted risk of this instability increasing over time.

The nutritional compositions according to the invention exhibit a content of total reducing substances which is less than or equal to 0.9% by weight based on the weight of the dry matter of the compositions, preferably less than or equal to 0.5%, and even more preferably less than or equal to 0.2%.

The invention relates, secondly, to a process for obtaining a nutritional composition which results from steeping maize and which possesses the abovementioned characteristics.

This process consists in treating the maize-steeping water, to which viable lactic acid bacteria have been added, with at least one protease and at least one phytase.

Surprisingly and unexpectedly, the Applicant Company demonstrated that a combined treatment of the maize-steeping water with at least one protease and at least one phytase in the presence of added viable lactic acid bacteria yielded particularly advantageous results which the skilled person could not logically have expected. Thus, the results of such a treatment do not simply correspond to the sum of the effects obtained by treating with a protease, those obtained by treating with a phytase and those obtained after simple addition of lactic acid bacteria.

The Applicant Company was furthermore able to demonstrate that the lactic acid bacteria which were introduced into the steeping water consumed reducing substances which were released following the enzyme treatment. More precisely, these reducing substances appear to result from secondary enzymic activities, such as amyloglucosidase, xylanase, cellulase and other hydrolases, which are present in commercial phytase and protease enzyme preparations of fungal origin.

Thus, the maize-steeping water into which viable lactic acid bacteria have been introduced, and which has been subjected to combined treatment with at least one protease and at least one phytase, exhibits both excellent nutritional characteristics and optimal microbiological stability.

The process according to the invention consists in introducing at least one protease and at least one phytase, simultaneously or consecutively, into the maize-steeping water, allowing them to act, while stirring, for a period which depends on the enzyme types and the quantities employed, introducing viable lactic acid bacteria into this steeping water, prior to, at the same time as or consecutive to the introduction of the enzymes, following, by taking samples, the change over time in the Pi/Pt ratio, the protein concentration and the content of total reducing substances, subsequently inactivating these enzymes and then concentrating the resulting composition by evaporation.

Treatment with enzymes is therefore an important step in the process according to the invention.

This treatment is carried out, following the step of steeping the maize, on steeping water which exhibits a dry matter content of between 5 and 25%, and preferably between 15 and 20%, a pH of between 3.0 and 5.0, and a temperature which varies between 40 and 50° C.

According to a preferred embodiment of the invention, the enzyme treatment will be applied to steeping water which has been obtained under the conditions described in French Patent No. 79 22106, which patent already presents a composition which is favourable for subsequent use in fermentation industries.

The order in which the enzymes are introduced is of little importance: thus, the treatment with protease can precede or follow the treatment with phytase. Similarly, the two types of enzyme can be employed simultaneously.

The quantities of enzyme which are used depend on the characteristic activity of the chosen enzyme and on the conditions for using it (type of substrate, concentration of the substrate, pH, temperature and duration of the treatment).

These quantities are between 0.1 and 2.0% based on the dry matter content of the medium, with regard to the protease, and between 0.01% and 0.1% with regard to the phytase, corresponding to a range of from 0.06 UA to 1.2 UA per 100 g of medium dry matter with regard to the protease and of from 50 to 500 UP per 100 g of medium dry matter with regard to the phytase.

The Anson unit (UA) is the protease unit, which is defined as being the quantity of enzyme which, at the optimum temperature and pH of this enzyme, hydrolyses haemoglobin to produce 1 micromole of tyrosine per minute in accordance with the calorimetric method employing the Folin Ciocalteu reagent. (For a detailed description of this method, reference can be made to the paper by M. L. ANSON which was published in 1939 in J. Gen. Physiol. 22, 79–89).

The phytase unit (UP unit) is defined as corresponding to the quantity of enzyme which, at a pH of 5.5 and a temperature of 37° C., releases one micromole of inorganic phosphorus per minute from a solution of sodium phytate having a concentration of 0.0015 mol/liter. (For a detailed description of this method, reference can be made to International Patent Application No. 93/16175).

The duration of the enzyme treatment varies between 4 and 16 hours.

The treatment is preferably carried out while stirring continuously.

The proteases which can be used in the process according to the invention are selected, in particular, from among the acid proteases such as those manufactured by BIOCON (ACID PROTEASE L B 59), by GIST BROCADES (PROTEASE A), by R6HM (COROLASE PS), by GENENCOR (PROTEASE B99) or by NOVO (FLAVOURZYME).

The protease treatment can also result from the actual presence, within the steeping water, of endogenous proteases, that is proteases which have been generated by the bacteria which have developed during the steeping operation.

Phytases which may be mentioned by way of example are FINASE, which is manufactured by ALKO, or NATU-PHOS 5000, which is marketed by BASF, or NOVO PHYTASE, which is marketed by NOVO.

Another important step in the process according to the invention consists in introducing viable lactic acid bacteria into the maize-steeping water.

Preferably, the lactic acid bacteria will be introduced prior to, or at the same time as, the enzyme treatment.

The lactic acid bacteria are introduced either by inoculating a culture of lactic acid bacteria or using lactic acid bacteria which have been obtained following concentration, in particular by centrifugation, from a medium containing them.

The culture of lactic acid bacteria can be obtained from lactic acid organisms of any species of the genus Lactobacillus, in particular *Lactobacillus delbrueckii* or *Lactobacillus leichmanii*. These lactic acid organisms are cultured on a liquid medium which is suitable for growing them, at 48° C. for at least 8 hours with gentle shaking. A 1 to 10% inoculum, according to their concentration, is introduced into the steeping water which has been subjected to the enzyme treatment.

The contact time between the lactic acid bacteria and the steeping water which has been subjected to the enzyme treatment shall be at least 8 hours.

Samples of the reaction medium are taken at regular intervals for the purpose of determining the concentrations of inorganic phosphorus and total phosphorus, the concentration of protein, by the C test, and the content of total reducing substances.

The enzyme reactions can be stopped by inactivating the enzymes when the Pi/Pt ratio reaches the minimum value of 35%, when the protein concentration, determined by the C test, becomes less than or equal to 5, and when the content of total reducing substances is less than or equal to 0.9%.

According to one preferred embodiment, the enzyme reactions shall be stopped when the Pi/Pt ratio reaches the value of 60%, or even more preferably 75%, when the protein concentration, determined by the C test, is less than or equal to 1 and even more preferably less than or equal to 0.5, and when the content of total reducing substances is less than or equal to 0.5% and even more preferably less than or equal to 0.2%.

Physical (temperature) and/or chemical (pH) means are used for inactivating the enzymes. Preferably, the reaction medium is heated at 80–100° C. for a time of between 10 and 30 minutes.

In order to eliminate the microorganisms, and in particular the lactic acid bacteria, which have been inactivated during the treatment for inactivating the enzymes, and in order to obtain a clear product in this way, the composition can be centrifuged or filtered through earth, through cloth or through a microfiltration or ultrafiltration membrane.

In order to improve the filterability, it is possible to add enzymes of the xylanase, hemicellulase or arabinoxylanase type, which enzymes hydrolyse the insoluble substances other than the proteins, the phytates and the lactic acid bacteria.

The process which is the subject of the present invention thus makes it possible to obtain a product whose dry matter content can reach 65%, something which affords numerous advantages, as previously described.

By virtue of their excellent nutritional characteristics and their improved stability, the compositions according to the invention are of particular relevance when used as fermentation substrates. Thus, they constitute a satisfactory substrate for producing yeasts, lactic acid bacteria or other microorganisms, and also enzymes, antibiotics, amino acids, organic acids, vitamins or biopesticides, under favourable conditions.

They are also particularly well suited for producing metabolites which are obtained using genetically modified microorganisms.

In addition, they are of interest to the food-stuff industry on account of their nutritional properties and their flavouring properties, and can thus be used as a foodstuff or as flavour enhancers in compositions which are intended for human or animal nutrition.

Finally, their nutritional characteristics render them entirely suitable for use in the preparation of fertilizers which are intended for plants.

The examples which are given below illustrate the invention without, however, limiting it.

EXAMPLE 1

Production of two nutritional compositions according to the invention.

Composition 1A:

1.5 liters of corn steep, having a dry matter content of 200 g/l, are introduced into a 2 liter reactor which is equipped with means for stirring and for regulating the temperature. The temperature of the substrate is adjusted to 48° C. and the stirring is adjusted to 200 rpm. The pH of the product is not adjusted and therefore remains at the natural pH of the corn steep or approximately 4.2.

A culture of lactic acid bacteria is then prepared from the strain *Lactobacillus delbrueckii* in accordance with the following protocol. This strain, which is kept on MRS (MAN-ROGOSA-SHARP) agar medium marketed by BIOKAR DIAGNOSTICS, and which has previously been cultured at 48° C., is used to seed 100 ml of culture medium which has been prepared by adding 1% yeast extract, 2% glucose and 0.5% calcium carbonate to demineralized water. This medium, having been introduced into a conical flask, is placed at 48° C., with gentle shaking, for 8 hours.

This culture of lactic acid bacteria is then added to the corn steep.

One hour after adding the lactic acid bacteria, the phytase NATUPHOS 5000 (BASF) and the protease ACID PROTEASE LB59, which is produced by BIOCON, are introduced simultaneously in the amounts of 0.03% and 1.5%, respectively, based on the dry matter content of the substrate.

The total duration of the treatment is 16 hours, during which the changes in the Pi/Pt ratio, the protein concentration and the concentration of reducing substances are monitored by withdrawing samples of the reaction medium every 4 hours.

The enzyme and biological reactions are then inactivated by heating at 90° C. for 20 minutes and then cooling down to ambient temperature once again. The resulting product is then centrifuged at 20° C. and at a speed of 4500 g for 15 minutes. The pellet, which essentially consists of inactivated lactic acid bacteria, is discarded and the supernatant is concentrated on a laboratory evaporator down to a dry matter content of 50%. The resulting product is then cooled down once again to ambient temperature while being stirred.

The composition which is obtained by the above-described process has a Pi/Pt ratio of 79%.

The protein assay, which is carried out using the C test, gives a value of 0.25.

The assay of the reducing substances gives a value of 0.2%.

Composition 1B:

1.5 l of corn steep, having a dry matter content of 150 g/l, are introduced into a 2 l reactor which is equipped with means for stirring and for regulating the temperature. The temperature of the substrate is adjusted to 48° C. and the stirring is adjusted to 200 rpm. The pH of the product is not adjusted and therefore remains at the natural pH of the corn steep.

The following are added to this substrate:
  BASF NATUPHOS 5000 phytase at a rate of 0.03% based on the dry matter content of the substrate
  ACID PROTEASE LB59 protease, which is produced by BIOCON, in an amount of 1.5% based on the dry matter content of the substrate.

The enzyme reaction is then initiated. After 2 hours, lactic acid bacteria, which are obtained after concentrating by centrifugation 100 ml of steeping water derived from the last maize-steeping silo before evaporation, are added to the enzyme-treated corn steep. The total duration of this treatment is 16 hours, during which the changes in the Pi/Pt ratio, the protein concentration and the content of reducing substances are monitored by withdrawing reaction medium every 4 hours. The enzyme and biological reactions are then inactivated by heating at 90° C. for 20 min and then cooling down to ambient temperature once again.

The resulting product is then centrifuged at 20° C. and at a speed of 4500 g for 15 minutes. The pellet, which consists essentially of inactivated lactic acid bacteria, is discarded and the supernatant is concentrated on a laboratory evaporator down to a dry matter content of 50%.

The composition which is obtained by the above-described process has a Pi/Pt ratio of 78%, while the protein assay carried out using the C test gives a value of 0.2 and the assay of the reducing substances gives a value which is less than 0.25%.

EXAMPLE 2
Production of four compositions, 2A, 2B, 2C and 2D, using the prior art Composition 2A corresponds to a control corn steep which has a dry matter content of 200 g/l and which has not undergone any enzyme treatment or addition of lactic acid bacteria.

Composition 2B corresponds to a corn steep which has a dry matter content of 200 g/l and which has not undergone any enzyme treatment but to which has been added a culture of lactic acid bacteria which was obtained by the procedure which was followed for preparing composition 1A.

Composition 2C is obtained by the process described for obtaining composition 1A apart from the fact that only ACID PROTEASE LB 51 protease, produced by BIOCON, was added to the corn steep, at a rate of 1.5% based on the dry matter content of the substrate.

Composition 2D is obtained by the process described for obtaining composition 1A apart from the fact that only NATUPHOS 5000 (BASF) phytase was added to the corn steep, at a rate of 0.025% based on the dry matter content of the substrate.

The Pi/Pt ratios, the protein concentrations measured by the C test, and the contents of total reducing substances (R.S.) of each of the four compositions 2A, 2B, 2C and 2D are given below.

|        | 2A  | 2B  | 2C   | 2D  |
|--------|-----|-----|------|-----|
| Pi/Pt  | 20  | 22  | 20   | 78  |
| Test C | 1.3 | 1.1 | 0.45 | 1.1 |
| R.S.   | 2   | 0.2 | 2.5  | 2.7 |

These four compositions are then concentrated down to a dry matter content of 50%.

EXAMPLE 3
Demonstration of the physical and microbiological stability of the nutritional compositions according to the invention 3a. Settling test Nutritional composition 1A according to the invention is subjected to a settling test, in which a comparison is made with the four compositions 2A, 2B, 2C and 2D described in Example 2.

This test consists in measuring the height of the deposit after allowing a previously sterilized composition to settle.

Composition 1A according to the invention, and compositions 2A, 2B, 2C and 2D, are first of all diluted to 25 g/liter, after which their pH is adjusted to a value of 7 by adding a 1 N solution of sodium hydroxide. This pH value corresponds to the maximum level of protein coagulation.

These compositions are then sterilized by being heated at a temperature of 120° C. for 20 minutes. After that, they are cooled down, homogenized and then introduced into graduated cylinders in which they are left to settle.

The height of the deposit in the case of each of the 5 compositions is measured after 30 minutes and after 16 hours. The following values, expressed in millimeters, were obtained:

| Composition     | 30 min | 16 hours |
|-----------------|--------|----------|
| 1A (Invention)  | 12     | 10       |
| 2A              | 170    | 85       |
| 2B              | 175    | 90       |
| 2C              | 160    | 80       |
| 2D              | 50     | 35       |

Perusal of these results clearly indicates the superiority of the composition according to the invention. Thus, the deposit is considerably reduced as compared with that which is observed after sterilizing each of the compositions according to the prior art.

3b. Coloration test

Nutritional composition 1A according to the invention is subjected to a coloration test, in which a comparison is made with the four compositions 2A, 2B, 2C and 2D described in Example 2.

This test consists in measuring the coloration of the compositions immediately after they have been concentrated down to 50% dry matter content and then after 1 month of storage at ambient temperature.

This measurement of coloration is carried out in the following manner. 10 g of the compositions, having a dry matter content of 50%, are introduced into 50 ml of distilled water. 75 ml of a 25 g/l solution of lead nitrate are then added. After stirring followed by filtration, the optical densities (D) are measured at 450 nanometers and 650 nanometers. The coloration is given by the formula:

$$O.D. = \frac{D(450 \text{ nm}) - D(650 \text{ nm})}{4} \times 160$$

The following values were obtained:

| Composition    | After concentration | After 1 month |
|----------------|---------------------|---------------|
| 1A (Invention) | 4.3                 | 4.9           |
| 2A             | 2.5                 | 7.2           |
| 2B             | 2.5                 | 3.2           |
| 2C             | 5.2                 | 8.4           |
| 2D             | 8.1                 | 16.3          |

A change in the colour during storage indicates that the product is physically unstable.

The composition according to the invention appears to be perfectly stable since its colour hardly changes after 1 month of storage, contrary to the compositions of the prior art.

3c. Microbiological stability test

Nutritional composition 1A according to the invention is subjected to a microbiological stability test, in which a comparison is made with the four compositions 2A, 2B, 2C and 2D described in Example 2. This test consists in counting the number of yeasts after storing the different compositions for 15 days at ambient temperature. The counting is carried out on OGA (oxytetracycline/glucose/agar) medium, which is marketed by BIOKAR DIAGNOSTICS, after incubating for 48 hours at 30° C. The following results, expressed in CFU (colony-forming units) per ml, were obtained:

| Composition | CFU/ml |
|---|---|
| 1A (Invention) | 100 |
| 2A | 1200 |
| 2B | 1850 |
| 2C | 80 |
| 2D | 1700 |

The excellent microbiological stability of the composition according to the invention, which only the known composition 2B can match in this regard, is evident from these results.

EXAMPLE 4

Application of the compositions according to the invention to the growth of microorganisms.

4a. The study described below consists in monitoring the increase in the number of cells as a function of time in culture media which contain a given concentration of nutritional composition 1A according to the invention, with comparison being made with culture media containing the same concentration of compositions 2A, 2B, 2C and 2D described in Example 2.

The study relates to the growth of a strain of *Bacillus subtilis*.

Culture media are prepared by adding glucose, at the rate of 10 g/l, and nutritional composition 1A, at a concentration of 2.6 g/l, to demineralized water. (This concentration of the nutritional composition corresponds to a nitrogen equivalent of 0.086 g/l). Culture media containing compositions 2A, 2B, 2C and 2D, described in Example 2, at a concentration of 2.6 g/l are prepared at the same time and in the same manner.

These culture media are then sterilized at 120° C. for 20 min.

100 ml of each of these media are then seeded with 0.1% by volume of a preculture of the strain.

Incubation is carried out at 30° C. for 24 hours while shaking at the rate of 280 revolutions per minute.

Counting is carried out on trypticase-soya agar medium (DIFCO) at the times 0, 8 hours and 24 hours.

The results which were obtained, and which are expressed in CFU (colony-forming units) per ml, are compiled in the following Table.

| | CFU/ml | | |
|---|---|---|---|
| Composition | 0h | 8h | 24h |
| 1A (Invention) | $1.9 \times 10^2$ | $7.3 \times 10^6$ | $2.6 \times 10^9$ |
| 2A | $1.1 \times 10^2$ | $2 \times 10^6$ | $1.6 \times 10^8$ |
| 2B | $1.25 \times 10^2$ | $2 \times 10^6$ | $1.9 \times 10^8$ |
| 2C | $1.5. \times 10^2$ | $3 \times 5.10^6$ | $5 \times 10^8$ |
| 2D | $1.9 \times 10^2$ | $6.2 \times 10^6$ | $10^9$ |

The results which were obtained demonstrate the particularly advantageous nutritional qualities of the composition according to the invention as compared with the compositions which do not exhibit the claimed characteristics.

4b. The study described below consists in monitoring the change in the growth of yeasts of the genus *Saccharomyces cerevisiae* by measuring glucose consumption and absorbance as a function of time in a culture medium containing a given concentration of nutritional composition 1A according to the invention, with comparison being made with a culture medium which contains the same concentration of nutritional composition 2A, described in Example 2.

The culture media are prepared by adding glucose, at the rate of 50 g/l, and nutritional composition 1A or 2A, at a concentration of 10 g/l, to demineralized water. The pH of each of these media is adjusted, before sterilization, to 5 by adding sodium hydroxide solution. The media are then sterilized at 120° C. for 20 min in 2 liter fermenters, with each fermenter containing 1.5 liters of medium.

Each fermenter is then seeded with 100 ml of a preculture of Saccharomyces cerevisiae, which preculture is contained in a 500 ml conical flask and obtained as follows: glucose, at the rate of 10 g/l, and yeast extracts, at the rate of 2 g/l, are added to demineralized water. After sterilization, this preculture medium is seeded with the *Saccharomyces cerevisiae* strain, which has been cultured on OGA agar medium. The medium is shaken on a shaker at 200 revolutions per minute, while being maintained at 30° C. for 8 hours.

After seeding, the fermenters are maintained at 30° C. and agitated at the rate of 1 v/v/min (volume of air per volume of medium per minute).

The absorbance and the glucose concentration are measured, for each medium, after 17 hours and after 24 hours.

The results which were obtained are compiled in the following Table:

| | 1A (Invention) | | 2A | |
|---|---|---|---|---|
| | Absorbance | Glucose in g/l | Absorbance | Glucose in g/l |
| 0h. | 0.4 | 40 | 0.6 | 40 |
| 17h. | 16.6 | 14 | 14 | 22 |
| 24h. | 25.5 | 0 | 20.7 | 8 |

The absorbance was measured at 620 nm on 1/50 dilutions. The values given above are the recorded absorbance multiplied by the dilution factor.

The results which were obtained demonstrate the excellent nutritional qualities of the composition according to the invention. Thus, it can be seen that the culture medium containing the nutritional composition according to the invention enables the yeast to grow at an accelerated rate, as expressed in a decrease in the concentration of glucose and an increase in the absorbance over time which are more rapid than when a culture medium is used which contains an untreated corn steep.

The totality of the results given in Examples 3 and 4 above demonstrates that it is only the compositions according to the invention which exhibit all the required qualities, both with regard to their physical stability and with regard to their microbiological stability, thereby making them compositions which possess excellent nutritional characteristics and which are perfectly suited to uses which require a sterilization step.

We claim:

1. Nutritional composition consisting essentially of fermented maize steepwater having an inorganic phosphorus concentration to total phosphorus concentration ratio (Pi/Pt) of between 35 and 95%, a protein concentration in a test C of less than or equal to 5, and a total reducing substances content in the BERTRAND method of less than or equal to 0.9% by weight based on the weight of dry matter of the composition.

2. Nutritional composition according to claim 1, having a Pi/Pt ratio between 60 and 95%, a protein concentration less than or equal to 1 and a total reducing substances content less than or equal to 0.5% by weight based on the weight of dry matter of the composition.

3. Nutritional composition according to claim 2, having a Pi/Pt ratio between 75 and 85%, a protein concentration less than or equal to 0.5, and a total reducing substances content in the BERTRAND method of less than or equal to 0.2% by weight based on the weight of dry matter of the composition.

4. Nutritional composition according to claim 1, having a dry matter content greater than or equal to 60% by weight based on the weight of any matter of the composition.

5. Process for producing a nutritional composition, said nutritional composition comprising an inorganic phosphorus concentration to total phosphorus concentration ratio (Pi/Pt) of between 35 and 95%, a protein concentration in a test C of less than or equal to 5, and a total reducing substances content in the BERTRAND method of less than or equal to 0.9%, said process comprising subjecting maize steepwater to a combined enzymatic-lactic acid bacteria treatment with at least one protease and at least one phytase in the presence of added viable lactic acid bacteria, and subsequently recovering the enzymatically-lactic acid bacteria treated maize steepwater as the nutritional composition.

6. Process according to claim 5, wherein the combined enzymatic-lactic acid bacteria treatment consists of:

a) introducing successively or simultaneously into the maize steepwater at least one protease, at least one phytase and at least lactic acid bacteria, b) allowing the protease, phytase and lactic acid bacteria to act, with stirring, c) monitoring, by sampling, variation over time of the Pi/Pt ratio, the protein concentration and the total reducing substances content, d) inactivating the protease, phytase and lactic acid bacteria, e) concentrating the steepwater from step d) by evaporation and, f) recovering the steepwater from step e) as the nutritional composition.

7. Process according to claim 5, wherein the combined enzymatic-lactic acid bacteria treatment is performed on a steepwater whose dry matter content is between 5 to 25% and pH between 3 and 5, at a temperature varying between 40 and 50° C., and for 4 to 16 hours.

8. Process according to claim 5, wherein the enzymatically-lactic acid bacteria treated maize water is centrifuged and then concentrated to a dry matter content greater than or equal to 60%.

9. A medium for culturing microorganisms and comprising the nutritional composition of claim 1.

10. A food or food additive for humans comprising the nutritional composition of claim 1.

11. A food or food additive for animals comprising the nutritional composition of claim 1.

12. A fertilizer for plants comprising the nutritional composition of claim 1.

* * * * *